US012765786B1

(12) United States Patent
Shaga

(10) Patent No.: US 12,765,786 B1
(45) Date of Patent: Oct. 20, 2026

(54) BLOOD PRESSURE DETERMINATION

(71) Applicant: Meta Platforms Technologies, LLC, Menlo Park, CA (US)

(72) Inventor: Ravi Krishna Shaga, Fremont, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 394 days.

(21) Appl. No.: 18/481,084

(22) Filed: Oct. 4, 2023

Related U.S. Application Data

(60) Provisional application No. 63/378,443, filed on Oct. 5, 2022.

(51) Int. Cl.

| | |
|---|---|
| ***A61B 5/021*** | (2006.01) |
| ***A61B 5/256*** | (2021.01) |
| ***A61B 5/397*** | (2021.01) |

(52) U.S. Cl.
CPC .......... *A61B 5/02108* (2013.01); *A61B 5/256* (2021.01); *A61B 5/397* (2021.01); *A61B 2560/02* (2013.01)

(58) Field of Classification Search
CPC ..... A61B 5/02108; A61B 5/256; A61B 5/397; A61B 2560/02
See application file for complete search history.

(56) References Cited

U.S. PATENT DOCUMENTS

| | | | | |
|---|---|---|---|---|
| 2017/0238812 | A1* | 8/2017 | Atlas | A61B 5/0205 |
| 2017/0340219 | A1* | 11/2017 | Sullivan | A61B 5/6824 |
| 2017/0367596 | A1* | 12/2017 | Mehrotra | A61B 5/021 |
| 2019/0209028 | A1* | 7/2019 | Baxi | A61B 5/01 |
| 2023/0393397 | A1* | 12/2023 | Daley | G02B 27/017 |
| 2025/0032029 | A1* | 1/2025 | Zhou | A61B 5/313 |

* cited by examiner

*Primary Examiner* — Justin Xu
(74) *Attorney, Agent, or Firm* — FREESTONE INTELLECTUAL PROPERTY LAW PLLC; Aaron J. Visbeek

(57) ABSTRACT

Methods, systems, and media for determining blood pressure are provided. According to some methods, a method for determining blood pressure comprises: obtaining a first impedance cardiography (BioZ) signal from a first electromyography (EMG) electrode disposed proximate an artery of a wearer of a wrist-worn device and a photoplethysmography (PPG) signal using a PPG sensor of the wrist-worn device, wherein the first EMG electrode is disposed in or on a band of the wrist-worn device; identifying a time point in the first BioZ signal associated with a predetermined biomarker and a corresponding time point in the PPG signal associated with the predetermined biomarker; determining a time delay between the time point in the first BioZ signal and the corresponding time point in the PPG signal; and determining a blood pressure of the wearer of the wrist-worn device based at least in part on the time delay.

18 Claims, 8 Drawing Sheets

BLOOD PRESSURE DETERMINATION

RELATED APPLICATIONS

This application claims the benefit of U.S. Provisional Application No. 63/378,443, filed Oct. 5, 2022, which is assigned to the assignee hereof, and which is incorporated herein in its entirety for all purposes.

BACKGROUND

Accurate and non-invasive blood pressure measurements may be important, for example, to monitor cardiovascular heath, quickly identify blood pressure abnormalities that may portend a serious health issue, etc. Because blood pressure can vary substantially over the course of the day, quick and accurate measurements of blood pressure may be useful to allow people to monitor and track their health. However, accurate measurements of blood pressure, that are measured quickly and non-invasively, are difficult to obtain.

SUMMARY

According to some embodiments, methods, systems, and media for blood pressure determination are provided. In some embodiments, a method for blood pressure determination involves obtaining a first impedance cardiography (BioZ) signal from a first electromyography (EMG) electrode disposed proximate an artery of a wearer of a wrist-worn device and a photoplethysmography (PPG) signal using a PPG sensor of the wrist-worn device, wherein the first EMG electrode is disposed in or on a band of the wrist-worn device. The method may further involve identifying a time point in the first BioZ signal associated with a predetermined biomarker and a corresponding time point in the PPG signal associated with the predetermined biomarker. The method may further involve determining a time delay between the time point in the first BioZ signal and the corresponding time point in the PPG signal. The method may further involve determining a blood pressure of the wearer of the wrist-worn device based at least in part on the time delay.

In some examples, the first BioZ signal and the PPG signal are obtained without active participation by the wearer of the wrist-worn device.

In some examples, the time delay reflects a pulse transit time between the artery of the wearer and capillary beds of the wearer.

In some examples, the artery of the wearer is one of an ulnar artery or a radial artery.

In some examples, the method further involves obtaining a second BioZ signal from a second EMG electrode disposed proximate to a second artery of the wearer of the wrist-worn device.

In some examples, more than two EMG electrodes are disposed in or on the band of the wrist-worn device. In some examples, the method further involves selecting at least one EMG electrode of the more than two EMG electrodes from which to obtain BioZ signals for use in determining the blood pressure of the wearer prior to obtaining the first BioZ signal. In some examples, selecting the at least one EMG electrode involves: obtaining BioZ signals from at least two of the more than two EMG electrodes; determining a variance over time of BioZ signals obtained from each of the at least two of the more than two EMG electrodes; and selecting the at least one EMG electrode based on the determined variance over time.

In some examples, the predetermined biomarker is a biomarker associated with an onset of a systolic phase of a cardiac cycle.

In some examples, the method further involves synchronizing the first BioZ signal and the PPG signal prior to determining the time delay.

In some embodiments, a wrist-worn device comprises: a first electromyography (EMG) electrode disposed in or on a band of the wrist-worn device, wherein the first EMG electrode is disposed proximate an artery of a wearer of a wrist-worn device; a photoplethysmography (PPG) sensor disposed in or on a portion of the wrist-worn device; and a controller. The controller may be configured to: obtain a first impedance cardiography (BioZ) signal from the first EMG electrode and a photoplethysmography (PPG) signal using the PPG sensor of the wrist-worn device; identify a time point in the first BioZ signal associated with a predetermined biomarker and a corresponding time point in the PPG signal associated with the predetermined biomarker; determine a time delay between the time point in the first BioZ signal and the corresponding time point in the PPG signal; and determine a blood pressure of the wearer of the wrist-worn device based at least in part on the time delay.

In some examples, the PPG sensor is disposed on a back side of a capsule of the wrist-worn device.

In some examples, the PPG sensor is configured to emit light in a green wavelength.

In some examples, the wrist-worn device further comprises a second EMG electrode disposed proximate to a second artery of the wearer of the wrist-worn device, wherein the second EMG electrode is disposed in or on the band of the wrist-worn device.

In some examples, more than two EMG electrodes are disposed in or on the band of the wrist-worn device.

In some examples, the first BioZ signal and the PPG signal are obtained without active participation by the wearer of the wrist-worn device.

In some examples, the controller is further configured to synchronize signals obtained from the first EMG electrode and signals obtained via the PPG sensors.

In some examples, the wrist-worn device further comprises an analog front end (AFE) circuit configured to receive and/or process both the first BioZ signal and the PPG signal.

In some examples, the wrist-worn device is configured to be associated with or paired with a virtual reality (VR) headset. In some examples, signals obtained from the first EMG electrode are usable by the VR headset.

BRIEF DESCRIPTION OF THE DRAWINGS

Illustrative embodiments are described in detail below with reference to the following figures.

Figure 1:
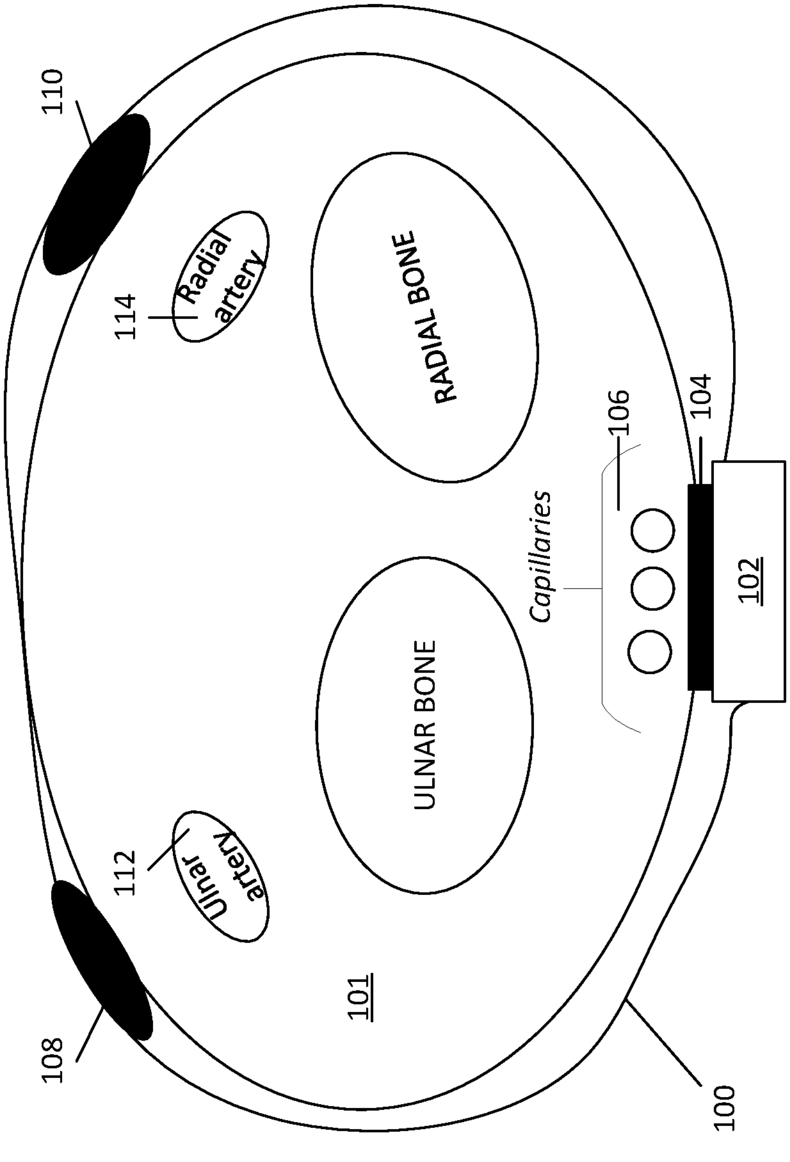
FIG. 1 is a diagram illustrating measurements of various physiological signals using a wrist-worn device in accordance with some embodiments.

The figures depict embodiments of the present disclosure for purposes of illustration only. One skilled in the art will readily recognize from the following description that alternative embodiments of the structures and methods illustrated may be employed without departing from the principles, or benefits touted, of this disclosure.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Accurate and non-invasive blood pressure measurements may be important, for example, to monitor cardiovascular heath, quickly identify blood pressure abnormalities that may portend a serious health issue, etc. Because blood pressure can vary substantially over the course of the day, quick and accurate measurements of blood pressure may be useful to allow people to monitor and track their health. Accordingly, being able to measure blood pressure via a wearable device, such as a smart watch, a ring, a patch, a head mounted device, smart glasses, or the like, is desirable. However, most techniques that have been attempted to measure blood pressure in wearable devices have struggled to measure blood pressure accurately.

Photoplethysmography (PPG) is a technique that measures blood volume, or blood volume changes, within blood vessels. PPG signals are acquired by emitting light toward tissue of a person (e.g., toward a fingertip, toward an earlobe, toward a wrist, etc.) and measuring characteristics of the light reflected back to a light detector. By characterizing the amount of reflected light, blood volume, or blood volume changes, may be determined.

Some techniques have attempted to measure blood pressure of a person using PPG. In particular, because a PPG signal may have characteristics of an arterial waveform, some techniques have attempted to determine blood pressure by measuring a first PPG signal that characterizes a blood vessel at a first location, and a second PPG signal that characterizes a blood vessel at a second location, and using a pulse transit time that reflects a delay between the first PPG signal and the second PPG signal. Because the pulse transit time is correlated with blood pressure, the time delay may be used to estimate blood pressure. However, accurately measuring the time delay (e.g., pulse transit time) using PPG alone may be difficult, because PPG signals (particularly those obtained using red and/or infrared light) may be corrupted by venous blood flow rather than solely measuring arterial blood.

Disclosed herein are methods, systems, media, and apparatuses for determining blood pressure of a wearer of a wrist-worn device. The wrist-worn device may be a smart watch, a fitness tracker, a bracelet, or the like. In particular, the wrist-worn device may have one or more electromyography (EMG) electrodes and one or more PPG sensors (e.g., including one or more light emitters and one or more light detectors). The light emitters may emit light in the green wavelength, which may preferentially probe surface level blood vessels such as capillaries. The EMG electrodes may be utilized to measure impedance cardiography (BioZ) signals, which may indicate blood volume changes in one or more arteries, such as a radial artery or an ulnar artery. A time delay between a reference point in the BioZ signal (which indicates arterial blood flow) and the corresponding reference point in the PPG signal (obtained using a wavelength that measures blood volume in the capillary beds) may be considered the pulse transit time for an arterial pulse to travel from the artery to the peripheral capillaries. The reference point may be a fiducial biomarker, such as a reference point associated with onset of a particular phase of the cardiac cycle. The time delay may then be used to determine blood pressure.

Note that the BioZ signals may be obtained using one or more EMG electrodes, where the one or more EMG electrodes may also (e.g., concurrently) be used to obtain EMG signals that indicate neuromuscular activity (e.g., of wrist flexor muscles or wrist extensor muscles). The EMG signals may be used for various functions, such as gesture detection. In some cases, the EMG signals may be used in conjunction with a paired virtual reality (VR) or augmented reality (AR) headset. In other words, the BioZ signals may be obtained using EMG electrodes that are additionally used for measuring EMG signals utilized for a purpose other than blood pressure determination.

FIG. 1 illustrates obtaining various physiological measurements using a wrist-worn device in accordance with some implementations. As illustrated, a wrist-worn device 100 may be worn by a wearer around the wrist. FIG. 1 illustrates a cross-section of the wrist 101. As illustrated, the ulnar bone, the radial bone, the ulnar artery, and the radial artery are within wrist 101. Wrist-worn device 100 includes a capsule 102. One end of capsule 102 (e.g., a top-facing portion that is not in contact with wrist 101) may include various features, such as a touchscreen or other display screen, various buttons, sliders, etc. The other end of capsule 102 may include a PPG sensor 104. PPG sensor 104 may include one or more light emitters (e.g., light-emitting diodes) and one or more light detectors. Depending on the wavelengths emitted by the light emitters of PPG sensor 104, changes in blood volume of relatively surface level blood vessels, such as capillaries 106, may be probed. For example, blood volume changes in capillaries 106 may be probed with green wavelength light.

As illustrated in FIG. 1, wrist-worn device 100 also includes EMG electrodes 108 and 110. EMG electrodes 108 and/or 110 may be disposed in or on a band of wrist-worn device 100, as shown in FIG. 1. EMG electrodes 108 and 110 may be dry electrodes configured to be in contact with the wearer's skin in order to measure neuromuscular activity, e.g., from wrist flexor and/or wrist extensor muscles. As illustrated, EMG electrode 108 is disposed proximate to ulnar artery 112, and EMG electrode 110 is disposed proximate to radial artery 114. Accordingly, a BioZ signal obtained from an EMG signal associated with EMG electrode 108 may reflect changes in blood volume within ulnar artery 112. Similarly, a BioZ signal obtained from an EMG signal associated with EMG electrode 110 may reflect changes in blood volume within radial artery 114.

It should be understood that although two EMG electrodes are illustrated in the wrist-worn device depicted in FIG. 1, in some implementations, a wrist-worn device may include any suitable number of EMG electrodes (e.g., one, two, four, eight, sixteen, etc.). In some embodiments, the techniques described herein may select a subset of the EMG electrodes from which BioZ signals are to be obtained, as shown in and described below in connection with FIG. 5.

In some embodiments, a blood pressure of a wearer of a wrist-worn device may be determined based on a time delay between a time point associated with a particular reference point in a BioZ signal and a time point associated with the corresponding reference point in a PPG signal. Because the BioZ signal may be acquired based on signals from an EMG electrode proximate to an artery (e.g., a radial artery and/or an ulnar artery), and because the PPG signal may be acquired using a wavelength that generally penetrates surface-level blood vessels such as capillaries, the time delay between the reference point in the BioZ signal and the corresponding reference point in the PPG signal may represent a pulse transit time, e.g., the time for the arterial pulse waveform to propagate from an artery to surface-level blood vessels such as capillaries. Because the pulse transit time is correlated with blood pressure, the blood pressure of the wearer of the wrist-worn device may be determined based on the pulse transit time. It should be noted that the reference point used to determine the time delay between the BioZ signal and the PPG signal may be any fiducial marker present in the BioZ signal and the PPG signal. Examples of reference points include the dicrotic notch, the point of maximum slope (which may indicate the onset of the systolic phase), or any other suitable reference point.

Figure 2:
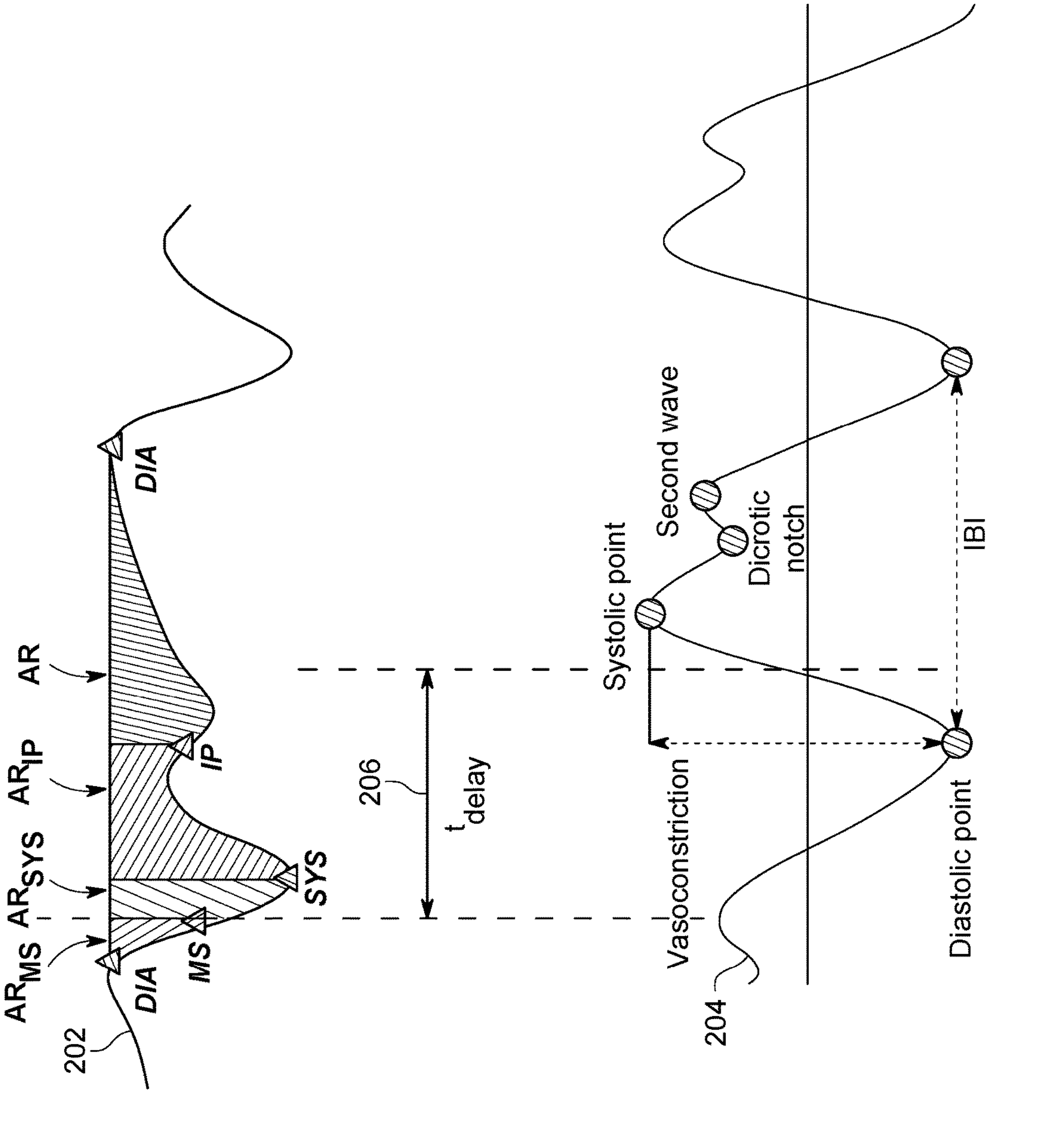
FIG. 2 is a diagram of an example impedance cardiography signal and an example photoplethysmography signal in accordance with some embodiments.

FIG. 2 illustrates an example BioZ signal 202 and an example PPG signal 204 with example reference points indicated. Note that, in the example shown in FIG. 2, a point of maximum slope in the BioZ signal and the corresponding point of maximum slope in the PPG signal is utilized to determine the time delay 206. The point of maximum slope may signify the onset of the systolic phase for a given cardiac cycle. Accordingly, when utilizing the point of maximum slope as the reference point by which the time delay is determined, the time delay may indicate the time delay between the onset of the systolic phase as seen at the artery versus as seen at the capillaries. However, other reference points may be utilized, as indicated in FIG. 2.

In some implementations, a wrist-worn device may have multiple (e.g., two, three, five, eight, sixteen, twenty, etc.) EMG electrodes. These EMG electrodes may be disposed in or on any portion of the wrist-worn device, including the capsule and the band. The EMG electrodes may be utilized for measurements other than BioZ signals, such as for measuring neuromuscular activity in the wrist extensor and/or wrist flexor muscles. In some implementations, the neuromuscular signals may be used for detecting gestures or movements made by the hand and/or the fingers of the wearer. In some embodiments, the wrist-worn device may be paired with or otherwise associated with a virtual reality or augmented reality headset or glasses, where the gestures made by the wearer's hand and/or fingers may be utilized in the virtual reality and/or augmented reality environment. In other words, the BioZ signals obtained using the EMG electrodes may be obtained using EMG electrodes that are also utilized for another purpose (e.g., gesture recognition) and/or by another device (e.g., a paired mobile phone, a paired tablet computer, a paired headset, etc.).

Figure 3A:
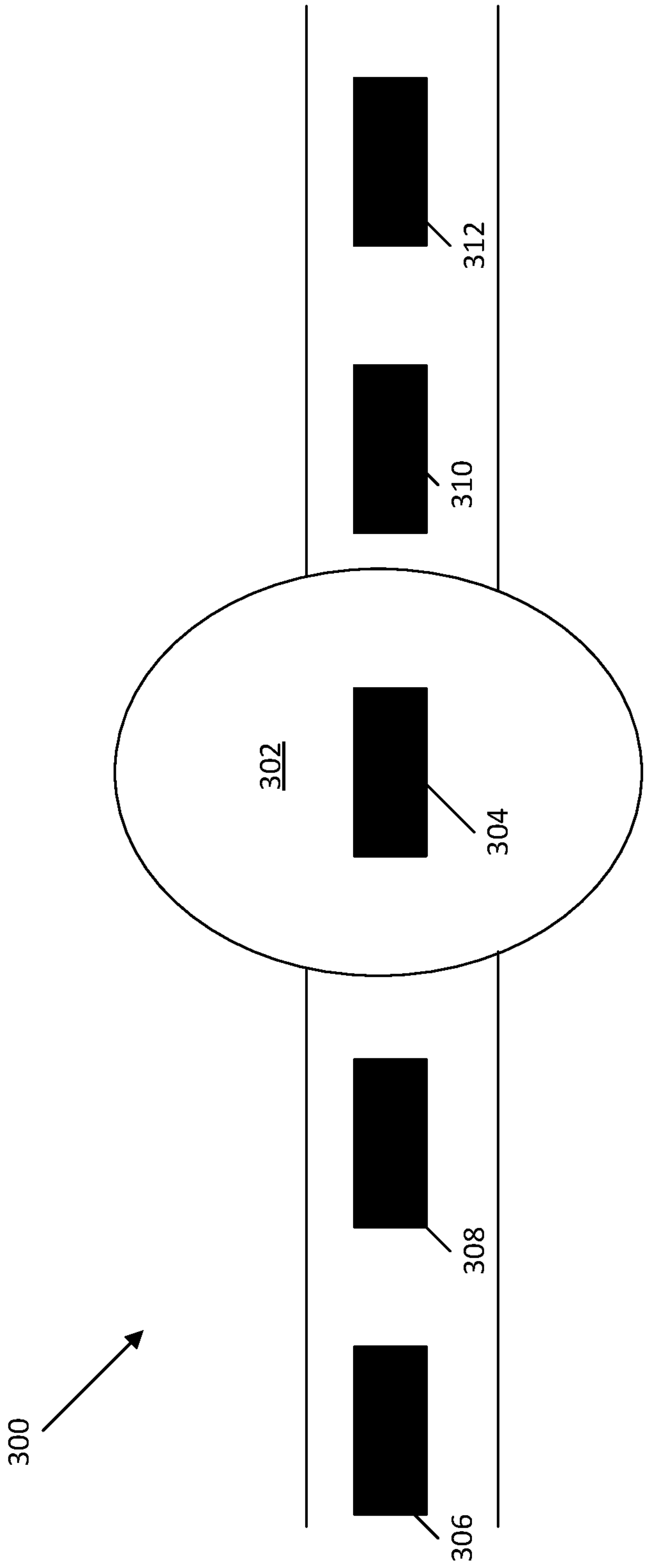
FIG. 3A is a schematic diagram of an example wrist-worn device in accordance with some embodiments.

FIG. 3A illustrates an example wrist-worn device 300 with multiple EMG electrodes. Note that FIG. 3A illustrates a backside portion of wrist-worn device 300 that is configured to be in contact with the skin of the wearer's wrist. As illustrated, wrist-worn device 300 includes a capsule 302. Capsule 302 includes a sensor 304, which may be a PPG sensor and/or an EMG electrode. Multiple sensors and/or electrodes may be disposed in or on capsule 302. The band of the wrist-worn device may include multiple EMG electrodes 306, 308, 310, and/or 312. Note that although the EMG electrodes are depicted as being linearly arranged along the band, in some implementations, the EMG electrodes may be in pairs along the band, and/or in any other suitable arrangement.

Figure 3B:
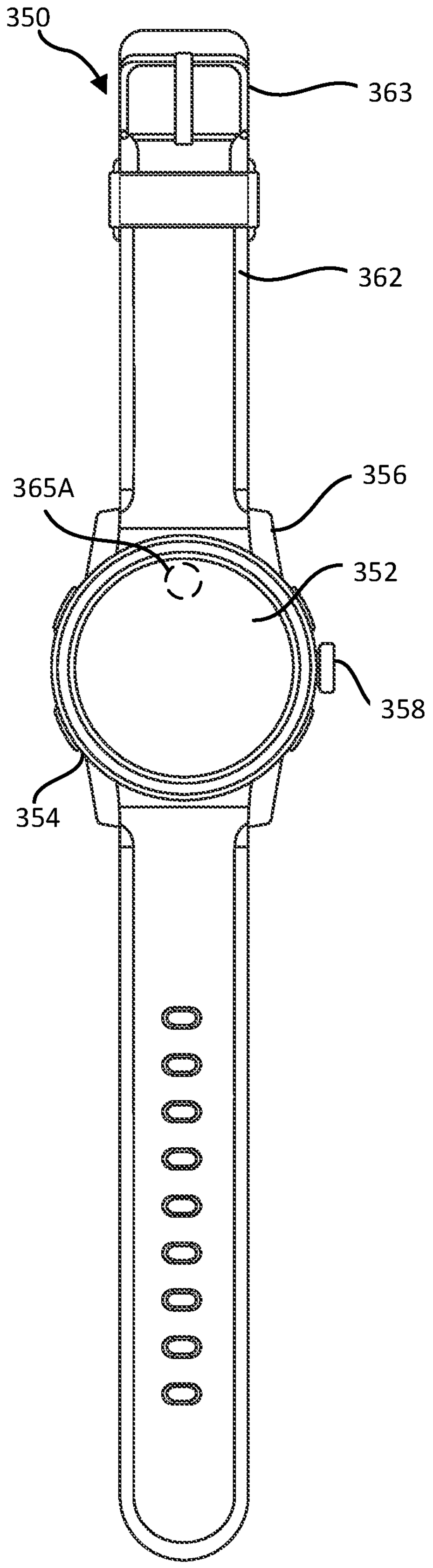
FIG. 3B is a plan view of an example wristband system in accordance with some embodiments.

As described above, in some implementations, the wrist-worn device may be a smart watch. FIG. 3B illustrates an example wristband system 350 that includes a watch body 354 coupled to a watch band 352. Watch body 354 and watch band 362 may have any size and/or shape that is configured to allow a user to wear wristband system 350 on a body part (e.g., a wrist). Wristband system 350 may include a retaining mechanism 363 (e.g., a buckle) for securing watch band 362 to the user's wrist. Wristband system 350 may perform various functions associated with the user. The functions may be executed independently in watch body 354, independently in watch band 362, and/or in communication between watch body 354 and watch band 362. Watch band 62 may be configured to operate independently (e.g., execute functions independently) from watch body 354. Additionally or alternatively, watch body 354 may be configured to operate independently (e.g., execute functions independently) from watch band 362. In some implementations, watch band 362 and/or watch body 354 may each include the independent resources required to independently execute functions. For example, watch band 362 and/or watch body 354 may each include a power source (e.g., a battery), a memory, data storage, a processor (e.g., a CPU), communications, a light source (e.g., at least one infrared LED for tracking watch body 364 and/or watch band 362 in space with an external sensor), and/or input/output devices.

In some implementations, the techniques described herein may obtain BioZ signals and corresponding PPG signals from a wearer of a wrist-worn device. The BioZ signals may be acquired from EMG electrodes proximate to an artery of the wearer, such as the radial artery and/or the ulnar artery. The PPG signal(s) may be acquired using light in a wavelength that penetrates at a particular depth. For example, in some embodiments, light may be in the green wavelength such that the light penetrates to a shallow depth and therefore, the corresponding PPG signal(s) may provide information regarding blood volume changes in surface level vessels (e.g., capillaries). A time point associated with a reference point, such as a fiducial biomarker, may be identified in the BioZ signal(s). A corresponding time point associated with the reference point may be identified in the PPG signal(s). A time delay between the identified time point in the BioZ signal and the identified time point in the PPG signal may be determined. This time delay may be considered to be, or correlated with, a pulse transit time, indicative of a time delay for an arterial pulse to travel from an artery to a capillary. The time delay may then be used to determine, or estimate, a blood pressure of the wearer.

Figure 4:
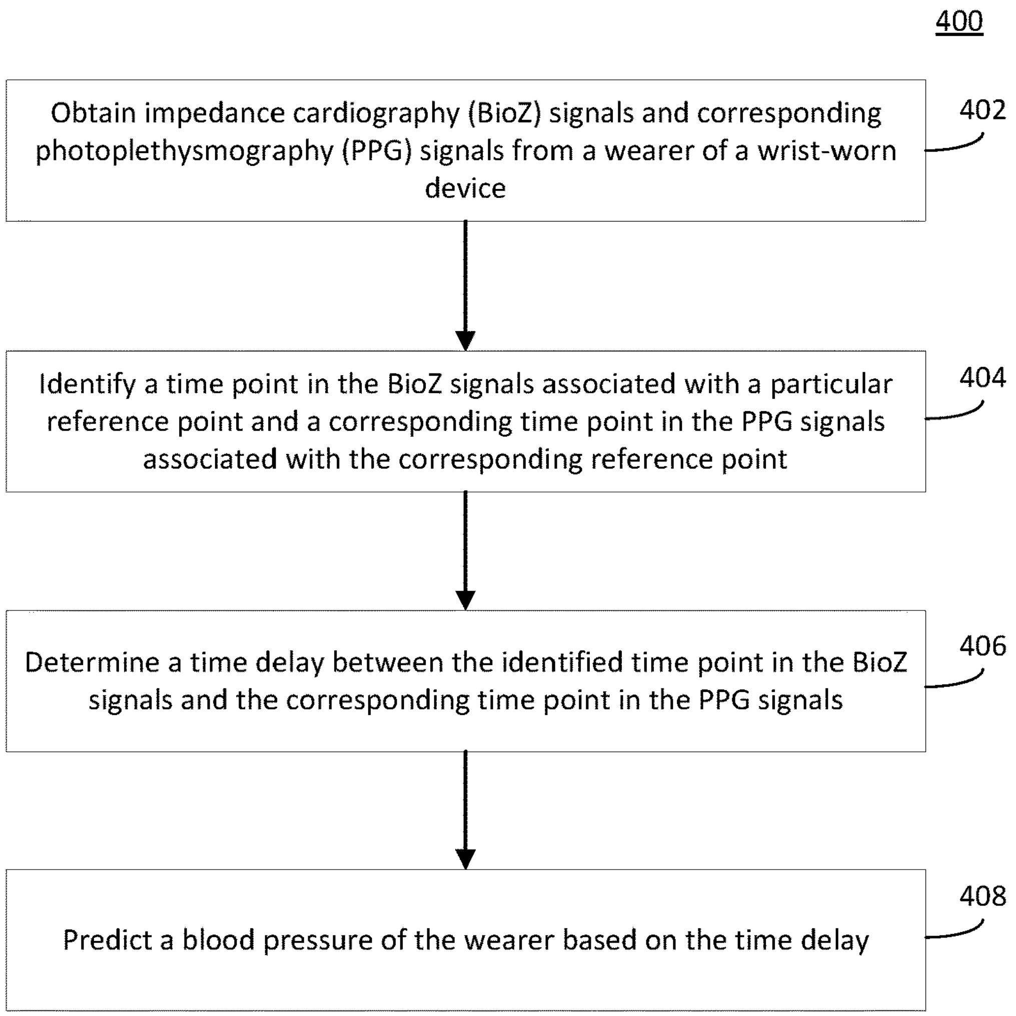
FIG. 4 is a flowchart of an example process for predicting a blood pressure of a wearer of a wrist-worn device in accordance with some embodiments.

FIG. 4 is a flowchart of an example process 400 for determining a blood pressure of a wearer of a wrist-worn device in accordance with some embodiments. In some implementations, blocks of process 400 may be executed by a processor of the wrist-worn device. In some embodiments, two or more blocks of process 400 may be executed substantially in parallel. In some embodiments, one or more blocks of process 400 may be omitted. In some implementations, blocks of process 400 may be performed in an order other than what is shown in FIG. 4.

Figure 5:
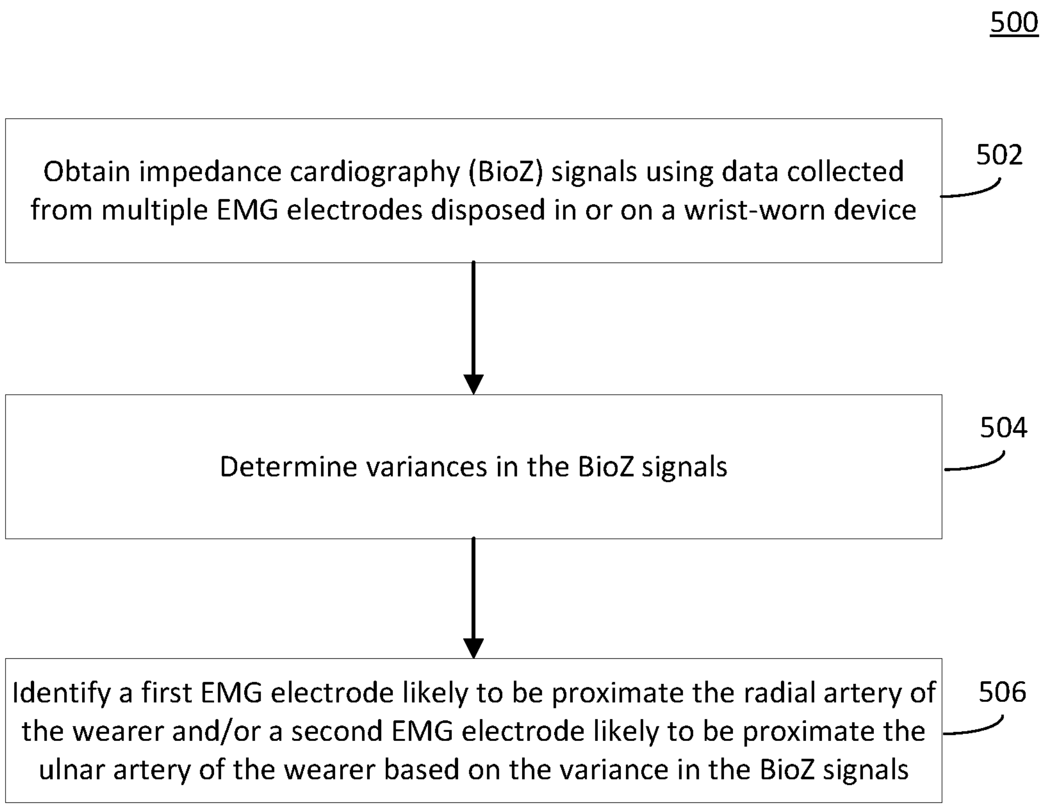
FIG. 5 is a flowchart of an example process for identifying electromyography electrodes to be used for obtaining impedance cardiography signals in accordance with some embodiments.

Process 400 can begin at 402 by obtaining BioZ signals and corresponding PPG signals associated with a wearer of a wrist-worn device. In some implementations, the BioZ signals may be acquired using one or more EMG electrodes disposed in or on a portion of the wrist-worn device (e.g., in or on a band of the wrist-worn device, in or on a back portion of a capsule of the wrist-worn device, etc.). In some embodiments, the EMG electrode(s) may be ones that are determined to be proximate to a radial artery and/or an ulnar artery of the wearer, and therefore the BioZ signals obtained from the EMG electrodes are reflective of blood volume changes in radial artery and/or the ulnar artery. Note that FIG. 5 illustrates a technique for selecting one or more EMG electrodes from which the obtain BioZ signals in accordance with some embodiments. Note that, although the EMG electrodes may be utilized to obtain EMG signals, which reflect voltage potentials associated with neuromuscular activity, the BioZ signals may be obtained by determining impedance information from signals recorded using the EMG electrodes. Changes in the BioZ signals as a function of time may reflect blood volume changes within the underlying blood vessels (e.g., within the ulnar artery and/or within the radial artery).

As described above, the PPG signals may be obtained using one or more light emitters and/or one or more light detectors of the wrist-worn device. In some implementations, the light emitter(s) and/or the light detector(s) may be disposed in or on the back portion of the capsule of the wrist-worn device that is proximate to and/or flush with the wrist of the wearer. In some implementations, the light emitted by the one or more light emitters may be in a wavelength that is known to penetrate relatively surface level vessels such as capillaries. For example, the light may be in a green wavelength.

Note that, in some implementations, a clock associated with acquisition of the BioZ signals may be synchronized to a clock associated with acquisition of the PPG signals in order to be able to accurate determine a time delay between corresponding reference points (as described below in connection with 406). In some such implementations, a synchronization protocol may be performed prior to acquisition of the BioZ signal and the PPG signal, e.g., as part of a power-on protocol of the wrist-worn device. Alternatively, in some implementations, the BioZ signal and the PPG signal may be acquired using a common analog front end (AFE) circuit or chip, which may obviate the need for clock synchronization.

At 404, process 400 may identify a time point in the BioZ signals associated with a particular reference point and a corresponding time point in the PPG signals associated with the corresponding reference point. The reference point may be any suitable biomarker indicative of a particular phase or phase onset of the cardiac cycle. An example may be the onset of the systolic phase, the onset of the diastolic phase, etc. Example reference points may be the point of maximum slope (which may correspond to the onset of the systolic phase), the dicrotic notch, or the like.

The time points in the BioZ signals and in the PPG signals may be identified using any suitable technique or combination of techniques. For example, in some embodiments, the time points may be identified using a template matching technique or algorithm configured to identify a particular point in the BioZ signal and/or in the PPG signal. As another example, in some implementations, the time points may be identified by providing the BioZ signal and/or the PPG signal to a trained machine learning model as inputs, where the trained machine learning model is configured to provide the time points as an output. As yet another example, in an instance in which the point of maximum slope is used as a reference point, the time points may be identified by determining an instantaneous slope for different points of the BioZ signal and/or the PPG signal, and identifying the maximum slope from the set of instantaneous slopes.

At 406, process 400 can determine a time delay between the identified time point in the BioZ signal and the corresponding time point in the PPG signal. For example, in some implementations, process 400 can subtract the time point associated with the PPG signal from the time point associated with the BioZ signal to determine the time delay. Note that, as described above, the time delay may be indicative of a pulse transit time from an artery (e.g., as measured using the BioZ signal) to the capillary (e.g., as measured using the PPG signal). In some implementations, the time delay may be within a range of about 10 milliseconds-100 milliseconds.

At 408, process 400 can predict a blood pressure of the wearer based on the time delay. In some embodiments, the blood pressure may include both a systolic blood pressure and a diastolic blood pressure. In some embodiments, the blood pressure may be determined or estimated by using the time delay as an input to a model or as a key value to a lookup table. For example, the time delay may be used as an input to a model (e.g., a regression model, a mathematical function, a neural network, etc.) that generates, as an output, the predicted blood pressure. As another example, the time delay may be used as a key to a look up table which identifies blood pressure values (e.g., systolic and diastolic) for the given time delay.

In some implementations, process 400 may present an indication of the blood pressure and/or store an indication of the blood pressure. For example, the blood pressure may be presented, e.g., on a display of the wrist-worn device. As another example, the blood pressure may be stored in a log file or other data file. The log file or data file may be stored locally in memory of the wrist-worn device and/or in memory of another device, such as a paired mobile phone or tablet computer, a cloud device, or any combination thereof.

In some implementations, a wrist-worn device may have multiple EMG electrodes (e.g., two, three, eight, ten, sixteen, twenty, etc.) which may be used to acquire BioZ signals. Because it may be important to utilize an EMG electrode proximate to the radial artery and/or the ulnar artery, an EMG electrode of the multiple EMG electrodes may be selected prior to acquiring the BioZ signals and the PPG signals used to determine the blood pressure of the wearer. For example, in some embodiments, the EMG electrode(s) to be used may be identified by obtaining BioZ signals from a set of candidate EMG electrodes. Continuing with this example, variations in the BioZ signals may be determined to identify, e.g., the EMG electrode which generates BioZ signals with a particular variance in the BioZ signal as a function of time. Because the BioZ signal reflects changes in the blood volume of the artery, the optimal EMG electrode to use (due to proximity to the radial artery and/or the ulnar artery) may be one that generates a BioZ signal with a variance as a function of time that is more than a threshold variance. For example, the optimal EMG electrode may be one that generates a BioZ signal having the largest variance as a function of time.

In some implementations, the set of candidate EMG electrodes may be a subset of the EMG electrodes of the wrist-worn device. For example, in some implementations, the set of candidate EMG electrodes may be selected using a priori knowledge of locations of the EMG electrodes of the wrist-worn device with respect to body regions of the wearer. As a more particular example, the a priori knowledge may indicate that a subset of the EMG electrodes (e.g., electrodes 7 and 8) are likely to be proximate to the radial artery of the wearer. Continuing with this more particular example, the techniques may select one of the subset of the EMG electrodes to use in acquiring BioZ signals for determining blood pressure by determining the variance associated with BioZ signals acquired from each of the subset of the EMG electrodes. By way of example, the variance of BioZ signals from electrode 7 and the variance of BioZ signals from electrode 8 may be determined, and the electrode for which BioZ signals have the larger variance may be selected as the EMG electrode to be used for acquiring BioZ signals for blood pressure determination.

FIG. 5 is an example of a process 500 for selecting EMG electrodes from a set of candidate EMG electrodes in accordance with some embodiments. In some implementations, blocks of process 500 may be executed by a processor of the wrist-worn device. In some embodiments, blocks of process 500 may be executed in an order other than what is shown in FIG. 5. In some embodiments, two or more blocks of process 500 may be executed substantially in parallel. In some embodiments, one or more blocks of process 500 may be omitted.

Process 500 can begin at 502 by obtaining BioZ signals using data collected from multiple EMG electrodes disposed in or on a wrist-worn device. The multiple EMG electrodes may be any suitable subset of the available EMG electrodes disposed in or on the wrist-worn device. For example, the multiple EMG electrodes may be a subset of the EMG electrodes of the wrist-worn device selected based on a priori knowledge of the location of a given EMG electrode with respect to the body of the wearer. As a more particular example, the EMG electrodes may be ones identified as likely to be proximate to a particular portion of the wearer's wrist (e.g., the right dorsal side, the left dorsal side, etc.) that is proximate to the radial artery and/or the ulnar artery.

At 504, process 500 can determine variances in the BioZ signals. For example, process 500 can determine, for each BioZ signal acquired using a given EMG electrode of the multiple EMG electrodes, a variance of the BioZ signal over time. Note that variance may refer to a statistical variance, or to any other suitable metric of variation over time.

At 506, process 500 can identify a first EMG electrode likely to be proximate the radial artery of the wearer and/or a second EMG electrode likely to be proximate the ulnar artery of the wearer based on the variance in the BioZ signals. For example, given a set of candidate EMG electrodes likely to be proximate to the radial artery, process 500 can select the EMG electrode that generates BioZ signals having the largest variance. As another example, given a set of candidate EMG electrodes likely to be proximate to the ulnar artery, process 500 can select the EMG electrode that generates BioZ signals having the largest variance. Note that, in some implementations, a first EMG electrode proximate the radial artery and a second EMG electrode proximate the ulnar artery may be identified. Alternatively, in some embodiments, only one EMG electrode proximate to either the radial artery or the ulnar artery may be identified. For example, the EMG electrode that generates BioZ signals having the largest variance may be identified, regardless of whether the EMG electrode is proximate the radial artery or the ulnar artery.

Figure 6:
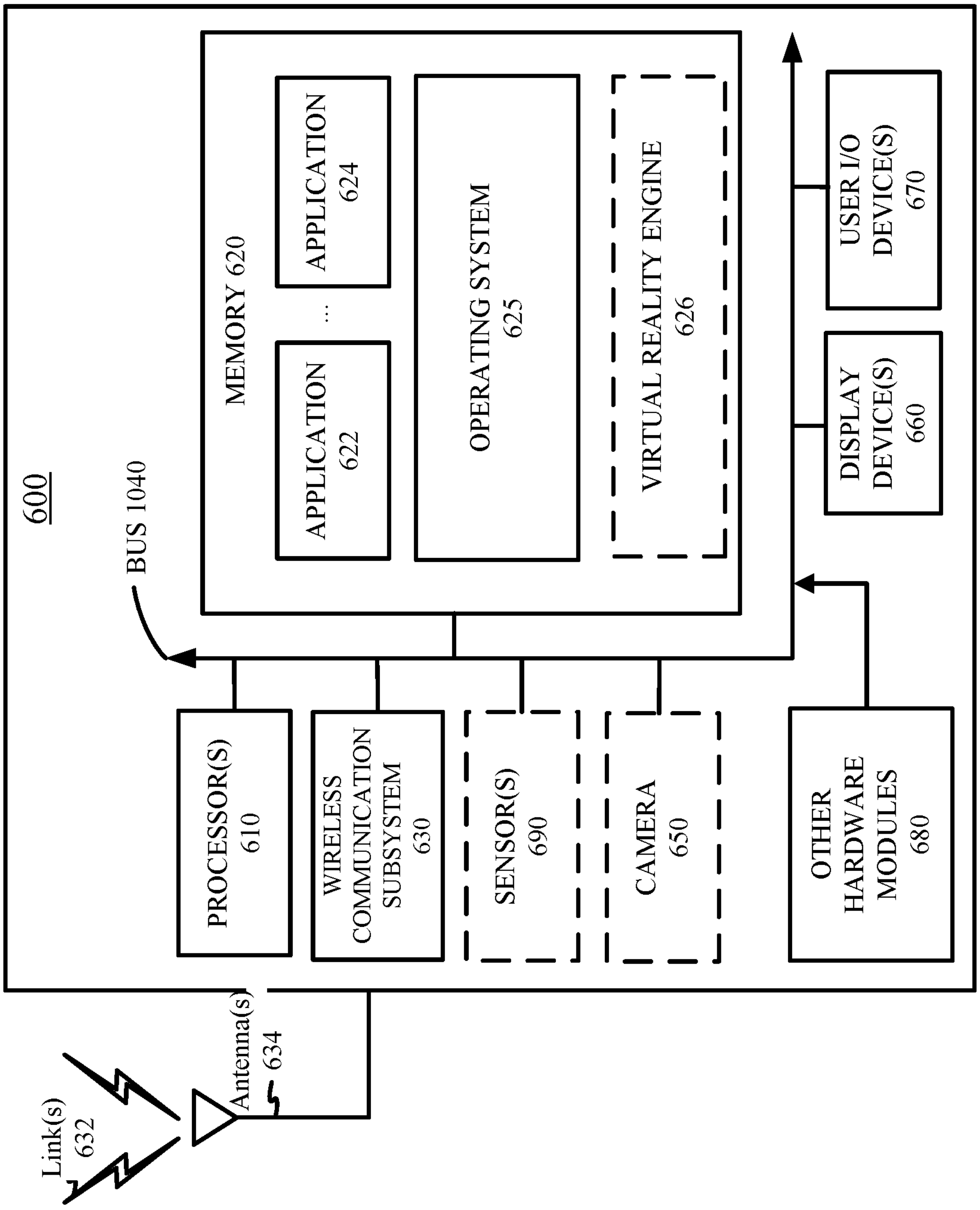
FIG. 6 is a simplified block diagram of an example of a computing system that may be implemented as part of a user device according to certain embodiments.

FIG. 6 is a simplified block diagram of an example of a computing system 600 for implementing some of the examples described herein. For example, in some embodiments, computing system may be used to implement a user device (e.g., a mobile phone, a tablet computer, a wrist-worn device, etc.) that implements the blocks of processes 400 and 400 of FIGS. 4 and 5, respectively. In the illustrated example, computing system 600 may include one or more processor(s) 610 and a memory 620. Processor(s) 610 may be configured to execute instructions for performing operations at a number of components, and can be, for example, a general-purpose processor or microprocessor suitable for implementation within a portable electronic device. Processor(s) 610 may be communicatively coupled with a plurality of components within computing system 600. To realize this communicative coupling, processor(s) 610 may communicate with the other illustrated components across a bus 640. Bus 640 may be any subsystem adapted to transfer data within computing system 600. Bus 640 may include a plurality of computer buses and additional circuitry to transfer data.

Memory 620 may be coupled to processor(s) 610. In some embodiments, memory 620 may offer both short-term and long-term storage and may be divided into several units. Memory 620 may be volatile, such as static random access memory (SRAM) and/or dynamic random access memory (DRAM) and/or non-volatile, such as read-only memory (ROM), flash memory, and the like. Furthermore, memory 620 may include removable storage devices, such as secure digital (SD) cards. Memory 620 may provide storage of computer-readable instructions, data structures, program modules, and other data for computing system 600. In some embodiments, memory 620 may be distributed into different hardware modules. A set of instructions and/or code might be stored on memory 620. The instructions might take the form of executable code that may be executable by computing system 600, and/or might take the form of source and/or installable code, which, upon compilation and/or installation on computing system 600 (e.g., using any of a variety of generally available compilers, installation programs, compression/decompression utilities, etc.), may take the form of executable code.

In some embodiments, memory 620 may store a plurality of application modules 622 through 624, which may include any number of applications. Examples of applications may include gaming applications, conferencing applications, video playback applications, or other suitable applications. The applications may include a depth sensing function or eye tracking function. Application modules 622-624 may include particular instructions to be executed by processor(s) 610. In some embodiments, certain applications or parts of application modules 622-624 may be executable by other hardware modules 680. In certain embodiments, memory 620 may additionally include secure memory, which may include additional security controls to prevent copying or other unauthorized access to secure information.

In some embodiments, memory 620 may include an operating system 625 loaded therein. Operating system 625 may be operable to initiate the execution of the instructions provided by application modules 622-624 and/or manage other hardware modules 680 as well as interfaces with a wireless communication subsystem 630 which may include one or more wireless transceivers. Operating system 625 may be adapted to perform other operations across the components of computing system 600 including threading, resource management, data storage control and other similar functionality.

Wireless communication subsystem 630 may include, for example, an infrared communication device, a wireless communication device and/or chipset (such as a Bluetooth® device, an IEEE 802.11 device, a Wi-Fi device, a WiMax device, cellular communication facilities, etc.), and/or similar communication interfaces. Computing system 600 may include one or more antennas 634 for wireless communication as part of wireless communication subsystem 630 or as a separate component coupled to any portion of the system. Depending on desired functionality, wireless communication subsystem 630 may include separate transceivers to communicate with base transceiver stations and other wireless devices and access points, which may include communicating with different data networks and/or network types, such as wireless wide-area networks (WWANs), wireless local area networks (WLANs), or wireless personal area networks (WPANs). A WWAN may be, for example, a WiMax (IEEE 802.17) network. A WLAN may be, for example, an IEEE 802.11x network. A WPAN may be, for example, a Bluetooth network, an IEEE 802.7x, or some other types of network. The techniques described herein may also be used for any combination of WWAN, WLAN, and/or WPAN. Wireless communications subsystem 630 may permit data to be exchanged with a network, other computer systems, and/or any other devices described herein. Wireless communication subsystem 630 may include a means for transmitting or receiving data, such as identifiers of HMD devices, position data, a geographic map, a heat map, photos, or videos, using antenna(s) 634 and wireless link(s) 632. Wireless communication subsystem 630, processor(s) 610, and memory 620 may together comprise at least a part of one or more of a means for performing some functions disclosed herein.

Embodiments of computing system 600 may also include one or more sensors 690. Sensor(s) 690 may include, for example, an image sensor, an accelerometer, a force sensor, a hydrostatic pressure sensor, a temperature sensor, a proximity sensor, a magnetometer, a gyroscope, an inertial sensor (e.g., a module that combines an accelerometer and a gyroscope), an ambient light sensor, or any other similar module operable to provide sensory output and/or receive sensory input, such as a depth sensor or a position sensor. For example, in some implementations, sensor(s) 690 may include one or more inertial measurement units (IMUs) and/or one or more position sensors. An IMU may generate calibration data indicating an estimated position of a device, based on measurement signals received from one or more of the position sensors. A position sensor may generate one or more measurement signals in response to motion of a device. Examples of the position sensors may include, but are not limited to, one or more accelerometers, one or more gyroscopes, one or more magnetometers, another suitable type of sensor that detects motion, a type of sensor used for error correction of the IMU, or some combination thereof. The position sensors may be located external to the IMU, internal to the IMU, or some combination thereof. At least some sensors may use a structured light pattern for sensing.

Computing system 600 may include a display module 660. Display module 660 may be a near-eye display, and may graphically present information, such as images, videos, and various instructions, from computing system 600 to a user. Such information may be derived from one or more application modules 622-624, virtual reality engine 626, one or more other hardware modules 680, a combination thereof, or any other suitable means for resolving graphical content for the user (e.g., by operating system 625). Display module 660 may use liquid crystal display (LCD) technology, light-emitting diode (LED) technology (including, for example, OLED, ILED, μLED, AMOLED, TOLED, etc.), light emitting polymer display (LPD) technology, or some other display technology.

Computing system 600 may include a user input/output module 670. User input/output module 670 may allow a user to send action requests to computing system 600. An action request may be a request to perform a particular action. For example, an action request may be to start or end an application or to perform a particular action within the application. User input/output module 670 may include one or more input devices. Example input devices may include a touchscreen, a touch pad, microphone(s), button(s), dial(s), switch(es), a keyboard, a mouse, a game controller, or any other suitable device for receiving action requests and communicating the received action requests to computing system 600. In some embodiments, user input/output module 670 may provide haptic feedback to the user in accordance with instructions received from computing system 600. For example, the haptic feedback may be provided when an action request is received or has been performed.

Computing system 600 may include a camera 650 that may be used to take photos or videos. Camera 650 may be configured to take photos or videos of the user. Camera 650 may also be used to take photos or videos of the environment, for example, for VR, AR, or MR applications. Camera 650 may include, for example, a complementary metal-oxide-semiconductor (CMOS) image sensor with a few millions or tens of millions of pixels. In some implementations, camera 650 may include two or more cameras that may be used to capture 3-D images.

In some embodiments, computing system 600 may include a plurality of other hardware modules 680. Each of other hardware modules 680 may be a physical module within computing system 600. While each of other hardware modules 680 may be permanently configured as a structure, some of other hardware modules 680 may be temporarily configured to perform specific functions or temporarily activated. Examples of other hardware modules 680 may include, for example, an audio output and/or input module (e.g., a microphone or speaker), a near field communication (NFC) module, a rechargeable battery, a battery management system, a wired/wireless battery charging system, etc. In some embodiments, one or more functions of other hardware modules 680 may be implemented in software.

In some embodiments, memory 620 of computing system 600 may also store a virtual reality engine 626. Virtual reality engine 626 may execute applications within computing system 600 and receive position information, acceleration information, velocity information, predicted future positions, or some combination thereof from the various sensors. In some embodiments, the information received by virtual reality engine 626 may be used for producing a signal (e.g., display instructions) to display module 660. For example, if the received information indicates that the user has looked to the left, virtual reality engine 626 may generate content that mirrors the user's movement in a virtual environment. Additionally, virtual reality engine 626 may perform an action within an application in response to an action request received from user input/output module 670 and provide feedback to the user. The provided feedback may be visual, audible, or haptic feedback. In some implementations, processor(s) 610 may include one or more GPUs that may execute virtual reality engine 626.

In various implementations, the above-described hardware and modules may be implemented on a single device or on multiple devices that can communicate with one another using wired or wireless connections. For example, in some implementations, some components or modules, such as GPUs, virtual reality engine 626, and applications (e.g., tracking application), may be implemented on two or more paired or connected devices.

In alternative configurations, different and/or additional components may be included in computing system 600. Similarly, functionality of one or more of the components can be distributed among the components in a manner different from the manner described above. For example, in some embodiments, computing system 600 may be modified to include other system environments, such as an AR system environment and/or an MR environment.

Figure 7:
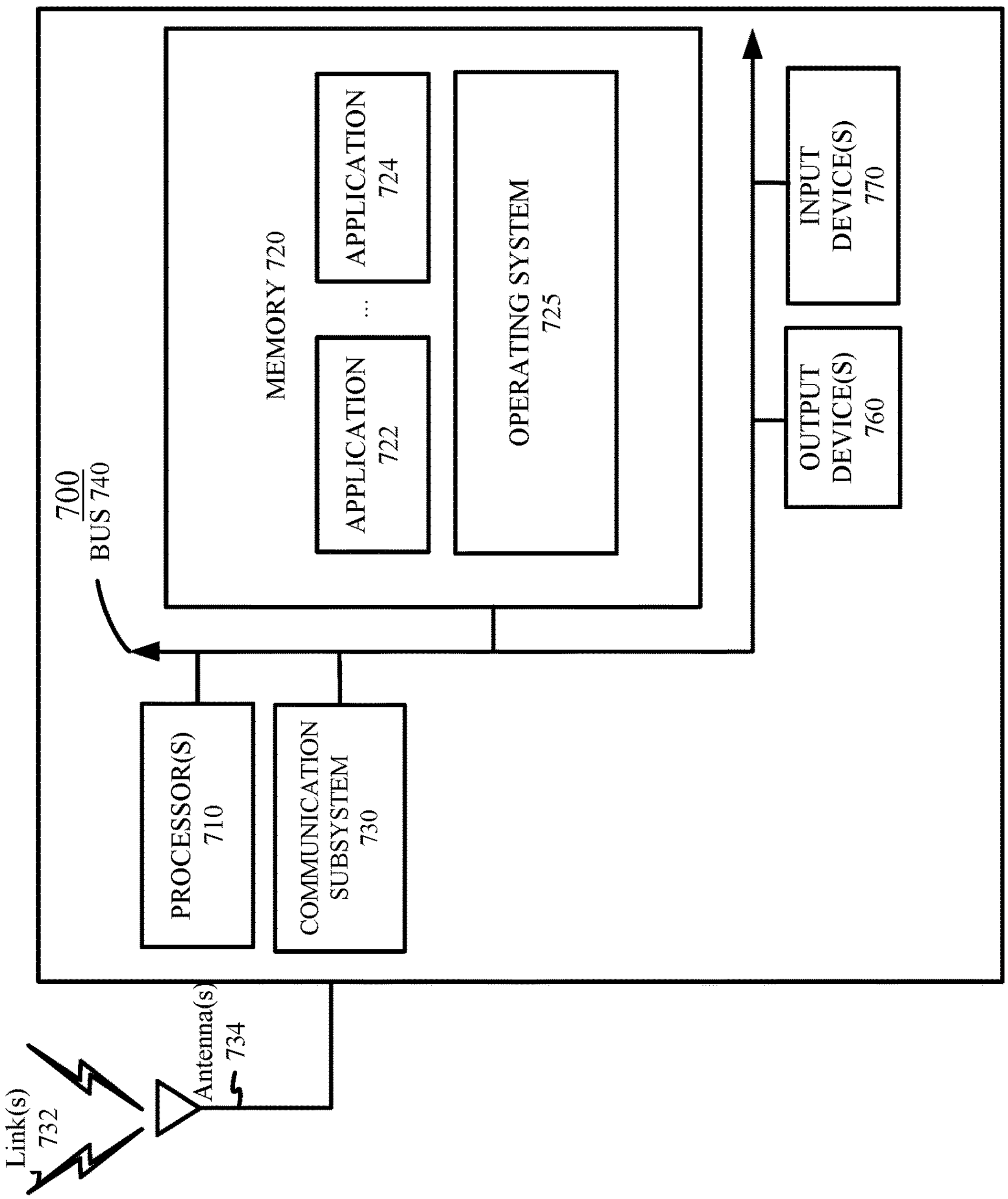
FIG. 7 is a simplified block diagram of an example of a computing system that may be implemented as part of a server according to certain embodiments.

FIG. 7 is a simplified block diagram of an example of a computing system 700 that may be implemented in connection with a server in accordance with some embodiments. For example, computing system 700 may be used to implement a server used to train a model, e.g., that relates pulse transit times to blood pressure, or the like.

In the illustrated example, computing system 700 may include one or more processor(s) 710 and a memory 720. Processor(s) 710 may be configured to execute instructions for performing operations at a number of components, and can be, for example, a general-purpose processor or microprocessor suitable for implementation within a portable electronic device. Processor(s) 710 may be communicatively coupled with a plurality of components within computing system 700. To realize this communicative coupling, processor(s) 710 may communicate with the other illustrated components across a bus 740. Bus 740 may be any subsystem adapted to transfer data within computing system 700. Bus 740 may include a plurality of computer buses and additional circuitry to transfer data.

Memory 720 may be coupled to processor(s) 710. In some embodiments, memory 720 may offer both short-term and long-term storage and may be divided into several units. Memory 720 may be volatile, such as static random access memory (SRAM) and/or dynamic random access memory (DRAM) and/or non-volatile, such as read-only memory (ROM), flash memory, and the like. Furthermore, memory 720 may include removable storage devices, such as secure digital (SD) cards. Memory 720 may provide storage of computer-readable instructions, data structures, program modules, and other data for computing system 700. In some embodiments, memory 720 may be distributed into different hardware modules. A set of instructions and/or code might be stored on memory 720. The instructions might take the form of executable code that may be executable by computing system 700, and/or might take the form of source and/or installable code, which, upon compilation and/or installation on computing system 700 (e.g., using any of a variety of generally available compilers, installation programs, compression/decompression utilities, etc.), may take the form of executable code.

In some embodiments, memory 720 may store a plurality of application modules 722 through 724, which may include any number of applications. Examples of applications may include gaming applications, conferencing applications, video playback applications, or other suitable applications. Application modules 722-724 may include particular instructions to be executed by processor(s) 710. In some embodiments, certain applications or parts of application modules 722-724 may be executable by other hardware modules. In certain embodiments, memory 720 may additionally include secure memory, which may include additional security controls to prevent copying or other unauthorized access to secure information.

In some embodiments, memory 720 may include an operating system 725 loaded therein. Operating system 725 may be operable to initiate the execution of the instructions provided by application modules 722-724 and/or manage other hardware modules as well as interfaces with a wireless communication subsystem 730 which may include one or more wireless transceivers. Operating system 725 may be adapted to perform other operations across the components of computing system 700 including threading, resource management, data storage control and other similar functionality.

Communication subsystem 730 may include, for example, an infrared communication device, a wireless communication device and/or chipset (such as a Bluetooth® device, an IEEE 802.11 device, a Wi-Fi device, a WiMax device, cellular communication facilities, etc.), a wired communication interface, and/or similar communication interfaces. Computing system 700 may include one or more antennas 734 for wireless communication as part of wireless communication subsystem 730 or as a separate component coupled to any portion of the system. Depending on desired functionality, communication subsystem 730 may include separate transceivers to communicate with base transceiver stations and other wireless devices and access points, which may include communicating with different data networks and/or network types, such as wireless wide-area networks (WWANs), wireless local area networks (WLANs), or wireless personal area networks (WPANs). A WWAN may be, for example, a WiMax (IEEE 802.17) network. A WLAN may be, for example, an IEEE 802.11x network. A WPAN may be, for example, a Bluetooth network, an IEEE 802.8x, or some other types of network. The techniques described herein may also be used for any combination of WWAN, WLAN, and/or WPAN. Communications subsystem 730 may permit data to be exchanged with a network, other computer systems, and/or any other devices described herein. Communication subsystem 730 may include a means for transmitting or receiving data, using antenna(s) 734, wireless link(s) 732, or a wired link. Communication subsystem 730, processor(s) 710, and memory 720 may together comprise at least a part of one or more of a means for performing some functions disclosed herein.

In some embodiments, computing system 700 may include one or more output device(s) 760 and/or one or more input device(s) 770. Output device(s) 770 and/or input device(s) 770 may be used to provide output information and/or receive input information.

Embodiments disclosed herein may be used to implement components of an artificial reality system or may be implemented in conjunction with an artificial reality system. Artificial reality is a form of reality that has been adjusted in some manner before presentation to a user, which may include, for example, a virtual reality, an augmented reality, a mixed reality, a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, for example, create content in an artificial reality and/or are otherwise used in (e.g., perform activities in) an artificial reality. The artificial reality system that provides the artificial reality content may be implemented on various platforms, including an HMD connected to a host computer system, a standalone HMD, a mobile device or computing system, or any other hardware platform capable of providing artificial reality content to one or more viewers.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

Specific details are given in the description to provide a thorough understanding of the embodiments. However, embodiments may be practiced without these specific details. For example, well-known circuits, processes, systems, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing various embodiments. Various changes may be made in the function and arrangement of elements without departing from the spirit and scope of the present disclosure.

Also, some embodiments were described as processes depicted as flow diagrams or block diagrams. Although each may describe the operations as a sequential process, many of the operations may be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It will be apparent to those skilled in the art that substantial variations may be made in accordance with specific requirements. For example, customized or special-purpose hardware might also be used, and/or particular elements might be implemented in hardware, software (including portable software, such as applets, etc.), or both. Further, connection to other computing devices such as network input/output devices may be employed.

With reference to the appended figures, components that can include memory can include non-transitory machine-readable media. The term "machine-readable medium" and "computer-readable medium" may refer to any storage medium that participates in providing data that causes a machine to operate in a specific fashion. In embodiments provided hereinabove, various machine-readable media might be involved in providing instructions/code to processing units and/or other device(s) for execution. Additionally or alternatively, the machine-readable media might be used to store and/or carry such instructions/code. In many implementations, a computer-readable medium is a physical and/or tangible storage medium. Such a medium may take many forms, including, but not limited to, non-volatile media, volatile media, and transmission media. Common forms of computer-readable media include, for example, magnetic and/or optical media such as compact disk (CD) or digital versatile disk (DVD), punch cards, paper tape, any other physical medium with patterns of holes, a RAM, a programmable read-only memory (PROM), an erasable programmable read-only memory (EPROM), a FLASH-EPROM, any other memory chip or cartridge, a carrier wave as described hereinafter, or any other medium from which a computer can read instructions and/or code. A computer program product may include code and/or machine-executable instructions that may represent a procedure, a function, a subprogram, a program, a routine, an application (App), a subroutine, a module, a software package, a class, or any combination of instructions, data structures, or program statements.

Those of skill in the art will appreciate that information and signals used to communicate the messages described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Terms, "and" and "or" as used herein, may include a variety of meanings that are also expected to depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein may be used to describe any feature, structure, or characteristic in the singular or may be used to describe some combination of features, structures, or characteristics. However, it should be noted that this is merely an illustrative example and claimed subject matter is not limited to this example. Furthermore, the term "at least one of" if used to associate a list, such as A, B, or C, can be interpreted to mean any combination of A, B, and/or C, such as A, AB, AC, BC, AA, ABC, AAB, AABBCCC, etc.

Further, while certain embodiments have been described using a particular combination of hardware and software, it should be recognized that other combinations of hardware and software are also possible. Certain embodiments may be implemented only in hardware, or only in software, or using combinations thereof. In one example, software may be implemented with a computer program product containing computer program code or instructions executable by one or more processors for performing any or all of the steps, operations, or processes described in this disclosure, where the computer program may be stored on a non-transitory computer readable medium. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques, including, but not limited to, conventional techniques for inter-process communications, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific embodiments have been described, these are not intended to be limiting. Various modifications and equivalents are within the scope of the following claims.

What is claimed is:

1. A method of determining blood pressure, the method comprising:

obtaining a first impedance cardiography (BioZ) signal from a first electromyography (EMG) electrode disposed proximate to an artery of a wearer of a wrist-worn device and a photoplethysmography (PPG) signal using a PPG sensor of the wrist-worn device, wherein the first EMG electrode is disposed in or on a band of the wrist-worn device;

identifying a time point in the first BioZ signal associated with a predetermined biomarker and a corresponding time point in the PPG signal associated with the predetermined biomarker;

determining a time delay between the time point in the first BioZ signal and the corresponding time point in the PPG signal; and determining a blood pressure of the wearer of the wrist-worn device based at least in part on the time delay, wherein the first EMG electrode is selected from at least two or more EMG electrodes located proximate to the radial artery or the ulnar artery and the selection is based at least in part on a comparison of variances in BioZ signals obtained from the at least two EMG electrodes, and wherein the BioZ signals determine impedance changes reflective of blood volume changes in the radial artery or the ulnar artery.

2. The method of claim 1, wherein the first BioZ signal and the PPG signal are obtained without active participation by the wearer of the wrist-worn device.

3. The method of claim 1, wherein the time delay reflects a pulse transit time between the artery of the wearer and capillary beds of the wearer.

4. The method of claim 1, wherein more than two EMG electrodes are disposed in or on the band of the wrist-worn device.

5. The method of claim 4, further comprising selecting the first EMG electrode based at least in part on the comparison of variances prior to obtaining the first BioZ signal from which to determine the blood pressure of the wearer.

6. The method of claim 5, wherein the comparison of variances of BioZ signals includes:

obtaining BioZ signals from the at least two or more EMG electrodes;

determining a variance over time of BioZ signals obtained from each of the at least two or more EMG electrodes; and selecting the first EMG electrode based on the determined variance over time.

7. The method of claim 1, wherein the predetermined biomarker is a biomarker associated with an onset of a systolic phase of a cardiac cycle.

8. The method of claim 1, further comprising synchronizing the first BioZ signal and the PPG signal prior to determining the time delay.

9. A wrist-worn device, comprising:

a first electromyography (EMG) electrode disposed in or on a band of the wrist-worn device, wherein the first EMG electrode is disposed proximate to an artery of a wearer of a wrist-worn device;

a photoplethysmography (PPG) sensor disposed in or on a portion of the wrist-worn device; and a controller configured to:

obtain a first impedance cardiography (BioZ) signal from the first EMG electrode and a photoplethysmography (PPG) signal using the PPG sensor of the wrist-worn device, identify a time point in the first BioZ signal associated with a predetermined biomarker and a corresponding time point in the PPG signal associated with the predetermined biomarker, determine a time delay between the time point in the first BioZ signal and the corresponding time point in the PPG signal, and determine a blood pressure of the wearer of the wrist-worn device based at least in part on the time delay, wherein the first EMG electrode is selected from at least two or more EMG electrodes located proximate to the radial artery or the ulnar artery and the selection is based at least in part on a comparison of variances in BioZ signals obtained from the at least two or more EMG electrodes, and wherein the BioZ signals determine impedance changes reflective of blood volume changes in the radial artery or the ulnar artery.

10. The wrist-worn device of claim 9, wherein the PPG sensor is disposed on a back side of a capsule of the wrist-worn device.

11. The wrist-worn device of claim 9, wherein the PPG sensor is configured to emit light in a green wavelength.

12. The wrist-worn device of claim 9, further comprising a second EMG electrode disposed proximate to a second artery including the radial artery or the ulnar artery of the wearer of the wrist-worn device, wherein the second EMG electrode is disposed in or on the band of the wrist-worn device.

13. The wrist-worn device of claim 9, wherein more than two EMG electrodes are disposed in or on the band of the wrist-worn device.

14. The wrist-worn device of claim 9, wherein the first BioZ signal and the PPG signal are obtained without active participation by the wearer of the wrist-worn device.

15. The wrist-worn device of claim 9, wherein the controller is further configured to synchronize signals obtained from the first EMG electrode and signals obtained via the PPG sensors.

16. The wrist-worn device of claim 9, further comprising an analog front end (AFE) circuit configured to receive and/or process both the first BioZ signal and the PPG signal.

17. The wrist-worn device of claim 9, wherein the wrist-worn device is configured to be associated with or paired with a virtual reality (VR) headset.

18. The wrist-worn device of claim 17, wherein signals obtained from the first EMG electrode are usable by the VR headset.

* * * * *